United States Patent [19]

Hartmann et al.

[11] 4,211,790
[45] Jul. 8, 1980

[54] COMBATING ARTHROPODS WITH AN OXIME ESTER OF N-CARBOXYLATED-CARBAMATE

[75] Inventors: Alfons Hartmann, Beckingen; Engelbert Kühle, Bergisch-Gladbach; Ingeborg Hammann, Cologne, all of Fed. Rep. of Germany

[73] Assignee: Bayer Aktiengesellschaft, Leverkusen, Fed. Rep. of Germany

[21] Appl. No.: 31,097

[22] Filed: Apr. 18, 1979

[30] Foreign Application Priority Data

May 10, 1978 [DE] Fed. Rep. of Germany ....... 2820360

[51] Int. Cl.² .................... C07D 307/86; A01N 9/12
[52] U.S. Cl. .................... 424/285; 260/346.73
[58] Field of Search .................... 260/346.73; 424/285

[56] References Cited

U.S. PATENT DOCUMENTS 3,857,860  12/1974  Kuhle et al. .................... 260/346.22

Primary Examiner—Henry R. Jiles
Assistant Examiner—Bernard Dentz
Attorney, Agent, or Firm—Sprung, Felfe, Horn, Lynch & Kramer

[57] ABSTRACT

The compound of the formula

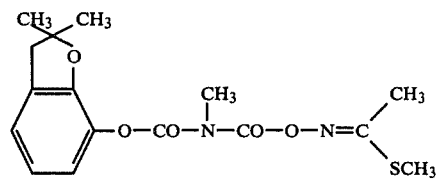

which possesses arthropodical activity.

4 Claims, No Drawings

COMBATING ARTHROPODS WITH AN OXIME ESTER OF N-CARBOXYLATED-CARBAMATE

The present invention relates to and has for its objects the provision of particular new N-carboxylated-carbamates which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It has already been disclosed that N-carboxylated N-methyl-carbamic acid aryl esters have insecticidal properties (see German Offenlegungsschrift No. 2,132,936). However, their action in many cases leaves something to be desired, above all when low concentrations are applied.

Furthermore, the carbamate S-methyl N-(methylcarbamoyloxy)thioacetamidate is known. Its action is also not completely satisfactory in all cases.

The present invention now provides, as a new compound, the N-carboxylated N-methyl-carbamic acid aryl ester of the formula

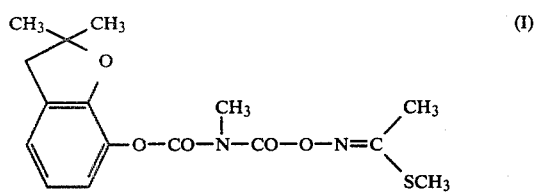

which has been found to possess powerful insecticidal properties.

It is surprising that the compound according to the invention exhibits a higher insecticidal potency than the N-carboxylated carbamates mentioned above and S-methyl N-(methylcarbamoyloxy)-thioacetamidate. These active compounds mentioned are related structurally. The new substance thus represents a valuable enrichment of the art.

The invention also provides a process for the preparation of the compound of the formula (I) in which N-chlorocarbonyl-N-methyl-2,2-dimethyl-2,3-dihydrobenzofuran-7-yl-carbamate, of the formula

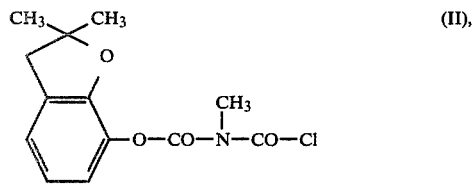

is reacted with N-hydroxyimidothioacetic acid S-methyl ester, of the formula

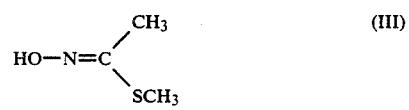

in the presence of an acid-binding agent and if appropriate in the presence of a diluent.

The course of the reaction can be represented by the equation which follows:

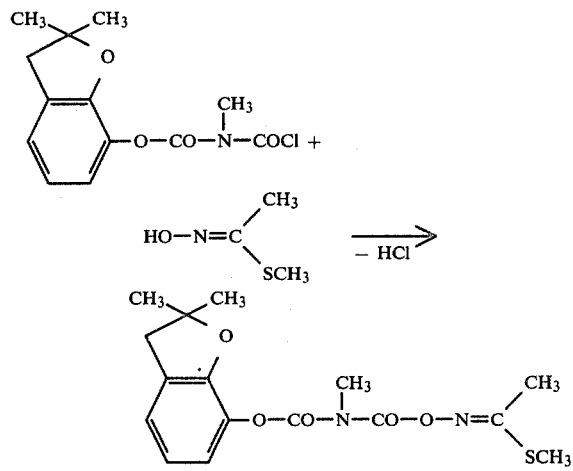

The starting compound (II) can be prepared by the process described in DE-OS (German Published Specification) No. 2,142,496 and can either be isolated in the pure form (melting point 63° C.) or can be reacted further in the form of the reaction mixture obtained, without isolation.

The starting compound (III) is described in DE-OS (German Published Specification) No. 1,568,646.

Suitable diluents for the preparation according to the invention are all the inert organic solvents. These include esters, such as diethyl ether, dioxane or tetrahydrofuran; hydrocarbons, such as benzene or toluene; chlorinated hydrocarbons, such as methylene chloride, chloroform or chlorobenzene; nitriles; esters; ketones; and mixtures of any of these solvents.

A tertiary organic base, for example triethylamine or benzyldimethylamine, is preferably added to the reaction mixture as the acid-binding agent.

The reaction temperature can be varied within a substantial range. In general, the reaction is carried out at from 0° to 100°, preferably at 10° to 60° C.

The reactants are usually employed in equimolar amounts.

The active compound is well tolerated by plants, has a favorable level of toxicity to warm-blooded animals and is suitable for combating arthropod pests, especially insects, which are encountered in agriculture, in forestry, in the protection of stored products and of materials, and in the hygiene field. It is active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae,*

*Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.

The active compound can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compound with extenders, that is to say liquid or liquified gaseous or solid diluents or carriers, optionally with the use of surfaceactive agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compound according to the invention may be used in the form of its formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compound may be employed in a customary manner appropriate for the particular use forms.

When used against pests harmful to health and pests of stored products, the active compound is distinguished by an excellent residual activity on wood and clay as well as a good stability to alkali on limed substrates.

In the veterinary field, the active compound according to the invention may be used in a known manner, such as orally in the form of, for example, tablets, capsules, drenches and granules; dermally by means of, for example, dipping, spraying, pouringon, spotting-on and powdering; and parenterally, for example by means of injections.

The present invention also provides an arthropodicidal composition containing as active ingredient the compound of the present invention in admixture with a solid or liquefied gaseous diluent or carrier or in admixture with a liquid diluent or carrier containing a surfaceactive agent.

The present invention also provides a method of combating arthropods, especially insects, which comprises applying to the arthropods, or to a habitat thereof, the compound of the present invention alone or in the form of a composition containing as active ingredient the compound of the present invention in admixture with a diluent or carrier.

The present invention also provides a method of freeing or protecting domesticated animals from parasitical insects which comprises applying to said animals the compound according to the present invention, in admixture with a diluent or carrier.

The present invention further provides crops protected from damage by arthropods by being grown in areas in which immediately prior to and/or during the time of the growing the compound of the present invention was applied alone or in admixture with a diluent or carrier.

It will be seen that the usual methods of providing a harvested crop may be improved by the present invention.

The present invention further provides domesticated animals whenever freed or protected from parasitical insects by the application to said animals of the compound according to the present invention, in admixture with a diluent or carrier.

Preparation of the novel compound is shown in the following illustrative example:

EXAMPLE 1

(a) 40.4 g (0.4 mol) of triethylamine were added dropwise to a solution of 65.6 g (0.4 mol) of 2,2-dimethyl-2,3-dihydrobenzofuran-7-ol and 62.4 g (0.4 mol) of N-bis-chlorocarbonyl-methylamine in 1.2 liters of toluene, while stirring. The mixture was stirred at room temperature for 8 hours, the amine hydrochloride which had precipitated was filtered off and the filtrate was evaporated in vacuo. The residue crystallized after a short time. It was stirred with petroleum ether and filtered off. 113.4 g of colorless crystals of N-chlorocarbonyl-N-methyl-2,2-dimethyl-2,3-dihydrobenzofuran-7-yl-carbamate of melting point 63° C. were obtained.

(b) 10.1 g (0.1 mol) of triethylamine were added dropwise to 28.35 g (0.1 mol) of N-chlorocarbonyl-N-methyl-2,2-dimethyl-2,3-dihydrobenzofuran-7-yl-carbamate and 10.5 g (0.1 mol) of N-hydroxyimidothioacetic acid S-methyl ester in 400 ml of toluene, while stirring. The mixture was stirred at room temperature for 5 hours and at 50° for 0.5 hour and extracted by shaking with water and the organic phase was dried over sodium sulphate and evaporated on a rotary evaporator. The oil which remained crystallized after some hours. It was stirred with a little ether/petroleum ether (1:1) and, after filtering the mixture, 36.4 g of colorless crystals of melting point 90° C., which were pure according to thin layer chromatography, were obtained.

The insecticidal activity of the compound of this invention is illustrated by the following examples:

EXAMPLE 2

Plutella test (long-term action after spraying)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*), which were about 10–15 cm high, were sprayed with the desired preparation of the active compound until dripping wet.

After the prescribed periods of time the plants were infested with caterpillars of the diamond-back moth (*Plutella maculipennis*). The destruction in % was determined at intervals of 3 days.

In this test, the compound of this invention showed a superior activity compared to the prior art.

EXAMPLE 3

Phaedon larvae test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into the preparation of the active compound of the desired concentration and were infested with mustard beetle larvae (*Phaedon cochleariae*), as long as the leaves were still wet.

After the specified periods of time, the degree of destruction was determined in %.

In this test the compound according to the invention showed a superior activity compared to the prior art.

It will be appreciated that the instant specification and examples are set forth by way of illustration and not limitation, and that various modifications and changes may be made without departing from the spirit and scope of the present invention.

What is claimed is:

1. The compound of the formula

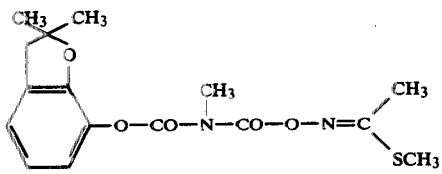

2. An arthropodical composition containing as active ingredient an arthropodicidally effective amount of the compound according to claim 1 in admixture with a diluent.

3. A method of combating arthropods which comprises applying to the arthropods, or to a habitat thereof, an arthropodicidally effective amount of the compound according to claim 1.

4. A method of freeing or protecting domesticated animals from parasitical insects which comprises applying to said animals an arthropodicidally effective amount of the compound according to claim 1.

* * * * *